(12) United States Patent
Kato et al.

(10) Patent No.: US 6,423,012 B1
(45) Date of Patent: Jul. 23, 2002

(54) MEDICAL GUIDE WIRE

(75) Inventors: Tomihisa Kato; Satoshi Nagano; Takashi Kato, all of Seto (JP)

(73) Assignee: Asahi Intecc Co., Ltd., Seto (JP)

( * ) Notice: Subject to any disclaimer, the term of this patent is extended or adjusted under 35 U.S.C. 154(b) by 0 days.

(21) Appl. No.: 09/621,002

(22) Filed: Jul. 20, 2000

(30) Foreign Application Priority Data

Jul. 21, 1999 (JP) ......................................... 2000-205835

(51) Int. Cl.⁷ ............................ A61B 5/00; A61M 25/00
(52) U.S. Cl. ......................................... 600/585; 600/434
(58) Field of Search ............................. 600/585, 433, 600/434, 435

(56) References Cited

U.S. PATENT DOCUMENTS

| | | | |
|---|---|---|---|
| 4,538,622 A | | 9/1985 | Samson et al. ............. 600/585 |
| 5,147,317 A | | 9/1992 | Shank et al. ................ 604/164 |
| 5,308,324 A | * | 5/1994 | Hammerslag et al. ....... 604/528 |
| 5,365,942 A | | 11/1994 | Shank ......................... 600/585 |
| 5,673,707 A | | 10/1997 | Chandrasekaran .......... 600/585 |
| 5,682,894 A | * | 11/1997 | Orr et al. ..................... 600/431 |
| 5,797,856 A | * | 8/1998 | Frisbie et al. ................ 600/585 |
| 5,865,768 A | * | 2/1999 | Orr .............................. 600/585 |
| 5,957,842 A | * | 9/1999 | Littmann et al. ............ 600/381 |

FOREIGN PATENT DOCUMENTS

| | | | |
|---|---|---|---|
| EP | 0 812 599 A | 12/1997 | .......... A61M/25/01 |
| JP | 4-25024 | 4/1992 | |
| JP | 4-292175 | 10/1992 | |

\* cited by examiner

Primary Examiner—John P. Lacyk
Assistant Examiner—Charles Marmor, II
(74) Attorney, Agent, or Firm—Morgan, Lewis & Bockius LLP

(57) ABSTRACT

A medical guide wire which is to ensure a good maneuverability when inserting its front end portion into blood vessels while turning the front end portion around its axis so as to provide an improved remedial treatment with patients. For this purpose, a core elongation has a torsional rigidity coefficient of 16 or less in terms of $K \times 10^3$. A helical spring has a helical diameter-to-line diameter ratio in the range of 2.5~3.5. Where the torsional rigidity coefficient is a divided value of (a maximum torsional stress based on a torsional moment to which the core member is subjected)/(the torsional moment to which the core member is subjected). The helical diameter-to-line diameter ratio is a value of (a mean value of outer and inner diameters of the helical spring)/(a line element diameter of the helical spring).

4 Claims, 2 Drawing Sheets

MEDICAL GUIDE WIRE

BACKGROUND OF THE INVENTION

1. Field of the Invention

The invention relates to a medical guide wire generally used as a catheter which is introduced into e.g., a cardiovascular system.

2. Description of the Prior Art

A medical guide wire has been used as a catheter to insert a very thin flexible tube into a blood vessel to take a picture of a vascular system. The medical guide wire has been also used as the catheter to insert a thin wire to place a balloon catheter at a specified blood vessel area so as to positively guide the balloon catheter safely when reopening a clogged coronary artery. These are illustrated by Japanese Provisional Patent Publication No. 4-25024 and Japanese Laid-open Patent Application No.4-292175.

By way of an example, a medical guide wire 1a (referred to as "guide wire" hereinafter) advances its front end portion 4a into a complicatedly curved blood vessel 6a or bifurcated blood vessel 7a as shown in FIG. 3. This requires a flexible property for the front end portion 4a, and at the same time, requiring a buckle resistant property against a load resisting in the direction which the guide wire 1a advances. The guide wire 1a is manipulated to turn around its axis at a handle portion 5a outside the body while advancing the front end portion 4a into the blood vessel 7a. This requires two mechanical properties. One is a corresponding torsional rigidity against the turning motion. The other is a favorable maneuverability to advance the front end portion 4a into the blood vessel 7a by the manipulating the handle portion 5a.

For this reason, the front end portion 4a includes a basic structure having a very thin core front wound by a helical spring.

Before inserting the guide wire 1a into the bifurcated blood vessel 7a, the front end portion 4a is plastically deformed manually into a hook-shaped configuration by way of illustration. When the hook-shaped portion 8a reaches near a bifurcation of the bifurcated blood vessel 7a, the guide wire 1a is turned around its axis to introduce the hook-shaped portion 8a into another path of the bifurcated blood vessel 7a as shown in FIG. 3. This manipulation enables operators to smoothly advance the front end portion 4a into the bifurcated blood vessel 7a.

In order to make the manipulation easier when introducing the front end portion 4a into the bifurcated blood vessel 7a, it is important to deform the hook-shaped portion 8a easily while ensuring a form-keeping property with the hook-shaped portion 8a. The hook-shaped portion 8a preferably has a property in which the front end portion 4a is easily deformed only in one specified direction, but has a corresponding rigidity in which the front end portion 4a resists to deform in directions other than the specified direction. In order to impart the bending property with the front end portion 4a, the front end portion 4a has been formed rectangular in cross section in which the front end portion 4a has a lateral length and a vertical length.

In the prior guide wire 1a, a priority has been put on the mechanical property that the very thin front end portion 4a is flexible and an outer diameter of the helical spring 3a generally confined to 0.355 mm. This structure is insufficient to impart an appropriate torsional rigidity with the core elongation which serves as a main role when transmitting an inserting force while turning the front end portion 4a around the axis. This may cause the front end portion 4a trapped in e.g., a blood vessel stricture area 9a to block the front end portion 4a from turning around the axis as shown in FIG. 5. This may torsionally deform the core elongation to eventually result in a rupture, which remains a ruptured piece inside the blood vessel.

When the helical spring 3a lacks the appropriate torsional rigidity upon moving in combination with the core elongation, a very thin line element W of the helical spring 3a may plastically deform wavily due to the torsional moment, thereby losing a smoothness of the line element W (FIG. 6) and expanding an outer diameter of the helical spring 3a. This may occur a lesion in a wall of the blood vessel due to the unfavorable deformation of the helical spring 3a engaging directly against the wall of the blood vessel.

When merely strengthening the torsional rigidity of the core elongation and the helical spring 3a in order to solve the above inconvenience, the maneuverability reduces to aggravate pains when inserting the core elongation into the blood vessel to give remedial measures to patients. Upon giving the remedial treatment on the coronary artery stricture area, a medical guide wire has been demanded which concurrently satisfies two conflicting requirements in which the front end portion 4a is sufficiently thin, while at the same time, having a torsional rigidity enough to timely respond to the turning motion transmitted from the handle portion 5a particularly when the front end portion 4a is stuck in the blood vessel stricture area.

Therefore, the present invention has been made with the above drawbacks in mind, it is a main object of the invention to provide a medical guide wire which is capable of satisfying the above two conflicting requirements simultaneously.

SUMMARY OF THE INVENTION

According to the present invention, there is provided a medical guide wire comprising: a core member having a flexible front end portion rectangular in cross section; a helical spring wound around the flexible front end portion of the core member; the core member having a torsional rigidity coefficient of 16 or less in terms of $K \times 10^3$; and the helical spring having a helical diameter-to-line diameter ratio in the range of 2.5~3.5. Where the torsional rigidity coefficient is a divided value of (a maximum torsional stress based on a torsional moment to which the core member is subjected)/(the torsional moment to which the core member is subjected), and the helical diameter-to-line diameter ratio is a value of (a mean value of outer and inner diameters of the helical spring)/(a line element diameter of the helical spring). In other words, the helical diameter means a distance from a center to a central line of the helical line element of the helical spring.

With the front end portion of the core member placed in the helical spring in which the outer diameter generally measures 0.355 mm, the front end portion is rectangular in cross section in the guide wire according to the invention. Considering the mechanical property that when inserting the core member into the blood vessel, the rigidity against the torsional moment to which the front end portion is subjected varies depending the lateral-to-vertical length ratio of the front end portion, an attention is paid to the torsional rigidity property of the core member. Such is the above structure as to overcome the technical problems i.e., "lack of the insufficient torsional rigidity which the front end portion has" and "unfavorable deformation to which the line element of the helical spring is subjected due to the torsional moment".

This is done based on experimental test results implemented with a multitude of medical guide wires employed herein.

In the medical guide wire according to the invention, the ratio of the vertical length to the lateral length of the front end of the core member is defined in the range of 1.25~1.75. This is to ensure a good maneuverability when inserting the front end portion into the blood vessel.

BRIEF DESCRIPTION OF THE DRAWINGS

Preferred forms of the present invention are illustrated in the accompanying drawings in which.

DETAILED DESCRIPTION OF THE PREFERRED EMBODIMENTS

Figure 1:
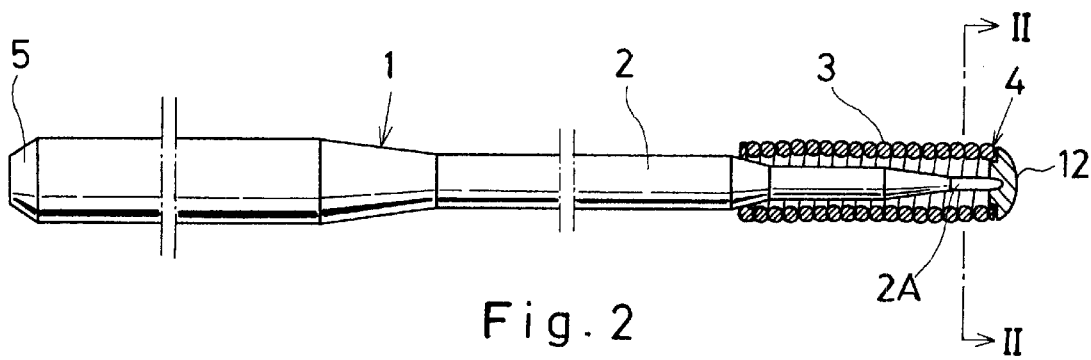
FIG. 1 is a plan view of a medical guide wire but partly sectioned.
Figure 2:
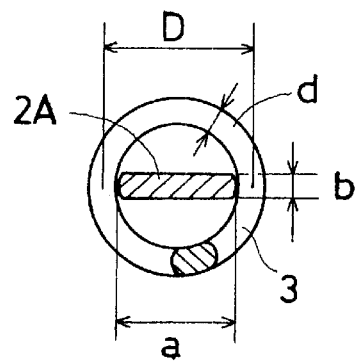
FIG. 2 is a cross sectional view of a front end portion of a core elongation taken along lines II—II of FIG. 1.
Figure 3:
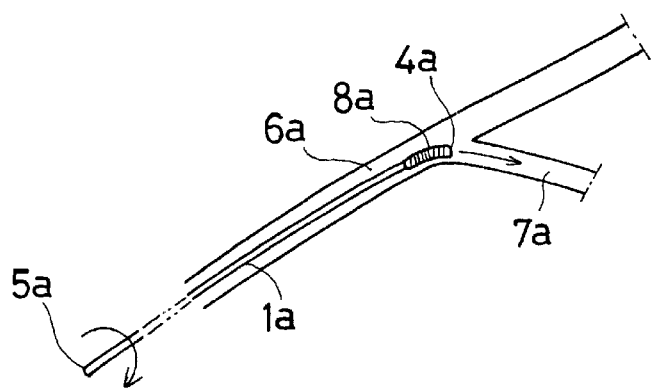
FIG. 3 is a schematic view of a prior medical guide wire in use for a blood vessel.

Referring to FIGS. 1 and 2 which show a medical guide wire 1 according to a first example of the invention, the medical guide wire 1 has a handle grip 5 and a core elongation 2 (core member) in which a front end portion 2A is wound by a helical spring 3 to form a leading head 4. The front end portion 2A rectangular in cross section has a lateral length (a=0.099 mm) and a vertical length (b=0.052 mm). A mean value (D) of outer and inner diameters of the helical spring 3 is 0.265 mm, and a line element diameter (d) measures 0.090 mm. From these numerical measurements, important factors are calculated as follows:

A torsional rigidity coefficient $K \times 10^3 \approx 14.7$

A helical diameter-to-line diameter ratio $(D/d) \approx 2.94$

A length ratio $(a/b) \approx 1.90$

Where the torsional rigidity coefficient is a divided value of (a maximum torsional stress based on a torsional moment to which the core elongation 2 is subjected)/(the torsional moment to which the core elongation 2 is subjected), and the helical diameter-to-line diameter ratio is a value of (the mean value (D) of the outer and inner diameters of the helical spring 3)/(the line element diameter (d) of the helical spring 3).

The above three formulas satisfy the torsional rigidity coefficient of 16 or less and the ratio (D/d) of 2.5~3.5 respectively.

As a second example of the invention, the front end portion 2A rectangular in cross section has the lateral length (a=0.093 mm) and the vertical length (b=0.070 mm). The mean value (D) of the outer and inner diameters of the helical spring 3 is 0.265 mm, and the line element diameter (d) measures 0.090 mm. Based on these numerical measurements, the important factors are calculated as follows:

A torsional rigidity coefficient $K \times 10^3 \approx 9.5$

A helical diameter-to-line diameter ratio $(D/d) \approx 2.94$

A length ratio $(a/b) \approx 1.329$

The above three formulas in turn satisfy the torsional rigidity coefficient of 16 or less, the ratio (D/d) of 2.5~3.5 and the length ratio (a/b) of 1.25~1.75.

As a third example of the invention, the front end portion 2A rectangular in cross section has the lateral length (a=0.101 mm) and the vertical length (b=0.079 mm). The mean value (D) of the outer and inner diameters of the helical spring 3 is 0.265 mm, and the line element diameter (d) measures 0.090 mm. Based on these numerical measurements, the important factors are calculated as follows:

A torsional rigidity coefficient $K \times 10^3 \approx 6.9$

A helical diameter-to-line diameter ratio $(D/d) \approx 2.94$

A length ratio $(a/b) \approx 1.278$

The above three formulas in turn satisfy the torsional rigidity coefficient of 16 or less, the ratio (D/d) of 2.5~3.5 and the length ratio (a/b) of 1.25~1.75.

As a fourth example of the invention, the front end portion 2A rectangular in cross section has the lateral length (a=0.107 mm) and the vertical length (b=0.067 mm). The mean value (D) of the outer and inner diameters of the helical spring 3 is 0.275 mm, and the line element diameter (d) measures 0.080 mm. Based on these numerical measurements, the important factors are calculated as follows:

A torsional rigidity coefficient $K \times 10^3 \approx 8.5$

A helical diameter-to-line diameter ratio $(D/d) \approx 3.43$

A length ratio $(a/b) \approx 1.597$

The above three formulas in turn satisfy the torsional rigidity coefficient of 16 or less, the ratio (D/d) of 2.5~3.5 and the length ratio (a/b) of 1.25~1.75.

Upon using the medical guide wire 1 for the remedial treatment for the blood vessel, no phenomena was appreciated that blocks the leading head 4 from turning around its axis, and plastically deforms the line element wavily when stuck in the blood vessel stricture area, thereby producing the medical guide wire of high quality substantially with no defects. The medical guide wires especially represented by the second through fourth examples have a good maneuverability upon inserting the leading head 4 into the blood vessel, whereby producing evidence that experimental test data correspond to the blood vessel treatment as described hereinafter in technical analyses.

The medical guide wire according to the invention is such that the core elongation 2 has the flexible property in the basic structure capable of a high trap load and blocking unfavorable deformation. This produces the high quality medical guide wire capable of the good maneuverability upon inserting the leading head 4 into the blood vessel while advantageously improving the blood vessel treatment further.

Figure 4:
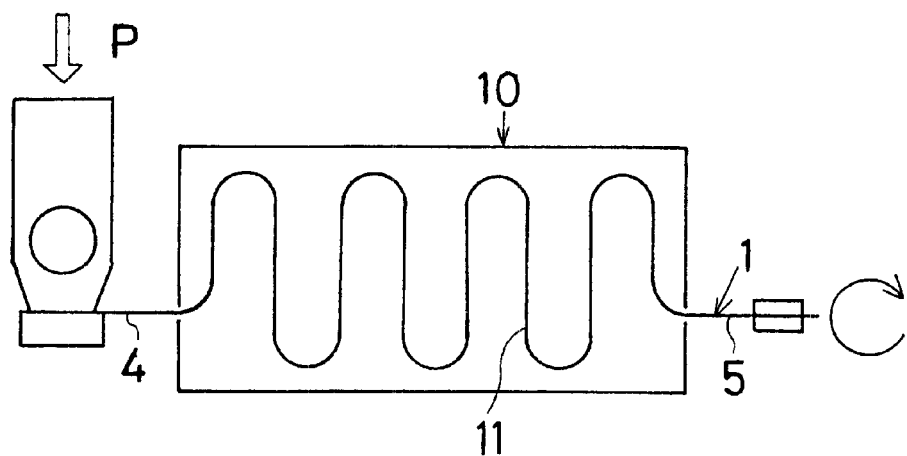
FIG. 4 is a schematic view of an experimental device to confirm that the medical guide is improved in its maneuverability.
Figure 5:
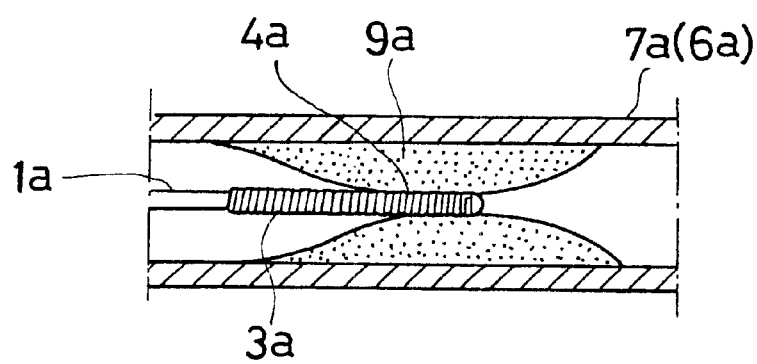
FIG. 5 is a schematic view of the prior medical guide wire in which a line element of a helical spring is wavily deformed due to a torsional moment to which the line element is subjected when inserting the front end portion into the blood vessel while turning the front end portion around its axis.
Figure 6:
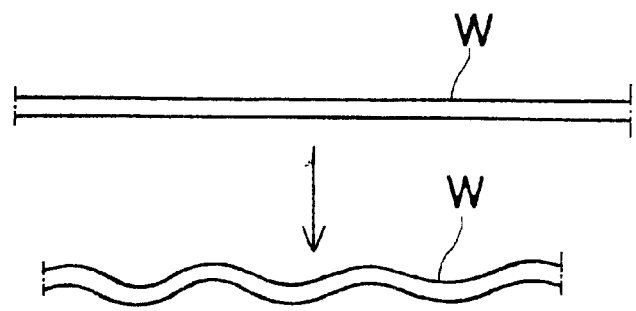
FIG. 6 is a schematic view of a prior art core elongation to show how the core elongation deforms due to a torsional moment.

The technical analyses has been done with a multitude number of guide wires usable for a human body employed herein in order to confirm the numerical definitions in the invention. The numerical definitions were adopted based on the experimental test data done with the use of the device 10 of FIG. 4. The experimental test device 10 has the severest requirements conceivable when inserting the medical guide wire for the blood vessel treatment. In the experimental test device 10, a serpentine mocking blood vessel path 11 is formed within a plastic plate to embed a plastic tube therein. The path 11 has both ends angularly turned 90° degrees while having seven middle main segments angularly turned 180° degrees alternately at 10 mm intervals. An inner diameter of the plastic tube measures 0.4 mm with no lubrication medium provided therein.

In order to confirm how the leading head 4 changes its torsional property depending the torsional rigidity coefficient K, a multitude of guide wires were prepared in which the leading heads 4 have different torsional rigidity coefficients K in order to insert the core elongations 2 into the plastic tube. With the use of the handle grip 5, the leading head 4 was turned around its axis in the same manner as when inserting the leading head 4 into the human blood vessel. Trap loads were determined when the leading head 4 came out of the plastic tube so that the leading head 4 has ceased its turning motion to observe a relativity between the trap load P and the torsional rigidity coefficient K.

Various rigidity coefficients K were determined by a wide variety of the combination of the lateral and vertical lengths (a, b). Two types of the line elements of the helical spring 3 were selected which have the diameters (d=0.090 mm, 0.072 mm) while determining the mean value (D) of the outer and inner diameters of the helical spring 3 to be 0.265 mm.

Table 1 shows the relativity between the trap load in P and the torsional rigidity coefficient K as the result of the experimental test. When the torsional rigidity coefficient ($K \times 10^3$) exceeds 16, the trap load P reduces substantially to a constant low level irrespective of the line element diameter (d) of the helical spring 3, which may block the leading head 4 from turning around its axis at the blood vessel stricture area. When the torsional rigidity coefficient ($K \times 10^3$) is 16 or less on the other hand, the trap load P increases rapidly to permit the leading head 4 turning around its axis continuously at the blood vessel stricture area.

TABLE 1

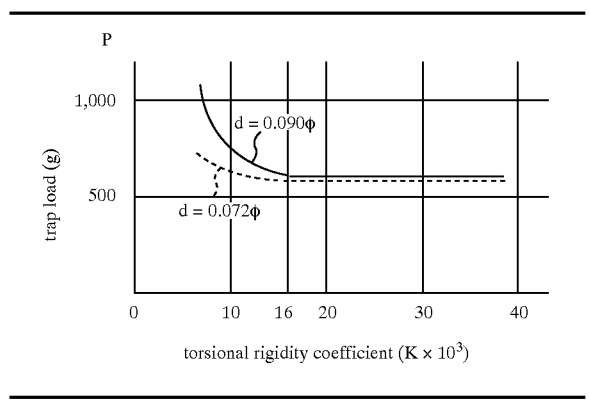

As a supplement, the torsional rigidity coefficient K is calculated based on the lateral length (a) and the vertical length (b) which the rectangular bar has at its cross section as observed at formulas in Table 2.

When the rectangular bar is subjected to a torsional moment T, a maximum torsional stress ($\tau$) occurs to the cross section of the rectangular bar.

$$\tau = T/(k_1 a\, b^2)$$

Where $k_1$ is a coefficient determined depending on (a/b).
$$k_1 = 1/\{3+1.8(b/a)\}$$

Based on the theory derived from the strength of materials, the torsional rigidity coefficient K is eventually expressed by the formula below.

$$K = \tau/T = 1/(k_1 a\, b^2) = \{3+1.8(b/a)\}/(a\, b^2)$$

In order to prevent the unfavorable deformation of the line element of the helical spring 3, the technical analysis was done based on the helical diameter-to-line diameter ratio (D/d) which is calculated by (the mean value (D) of the outer and inner diameters of the helical spring 3)/(the line element diameter (d) of the helical spring 3).

Table 3 shows how the wavy deformation occurs after maneuvering the medical guide wire on the experimental test device 10 in the same manner as when inserting the leading head 4 into the human blood vessel depending on the helical diameter-to-line diameter ratio (D/d). When the ratio is in the range of 2.5~3.5, it is apparently possible to effectively remove the wavy deformation of the line element of the helical spring 3. Based on the data, the numerical definition was adopted that the helical diameter-to-line diameter ratio (D/d) is in the range of 2.5~3.5. When the ratio (D/d) reduces to less than 2.5, a strong bending stress occurred on the line element invites defects such as cracks and flakes thereon upon manufacturing the helical spring 3, thus rendering it difficult to put the helical spring 3 into practical use. This is because the lower limit of the ratio (D/d) is 2.5.

TABLE 3

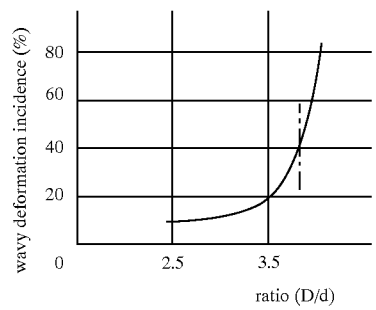

In order to ensure a good maneuverability when inserting the leading head 4 into the blood vessel, the numerical definition 1.25~1.75 of the length ratio (a/b) was adopted based on functional experimental test results below. Upon implementing the functional experimental test with the use of the experimental test device 10, several medical guide wires were prepared in which the length ratio (a/b) ranges from 1.0 to 2.5. Ten subject panelists were enrolled to experience their feeling by inserting the leading head 4 into the plastic tube of the experimental test device 10. The degree of the feeling was divided into five stages i.e., "good", "rather good", "normal", "not good" and "very bad" depending on the maneuverability which the subject panelists experienced. The length ratio (a/b) ranging from 1.25 to 1.75 was selected in which all the subject panelists had felt "good" or "rather good". The results of the functional experimental test are shown in Table 4.

TABLE 4

|  | a/b | | | | | | |
| --- | --- | --- | --- | --- | --- | --- | --- |
| panelists | 1.0 | 1.25 | 1.50 | 1.75 | 2.0 | 2.25 | 2.5 |
| 1 | C | A | AA | AA | A | B | D |
| 2 | C | A | AA | AA | B | C | D |
| 3 | C | A | A | AA | C | D | D |
| 4 | B | AA | AA | AA | A | B | C |
| 5 | C | A | A | AA | C | D | D |
| 6 | D | A | A | AA | A | C | D |
| 7 | C | A | AA | A | C | D | D |
| 8 | B | AA | AA | A | B | D | D |

TABLE 4-continued

| panelists | \[a/b\] | | | | | | |
|---|---|---|---|---|---|---|---|
| | 1.0 | 1.25 | 1.50 | 1.75 | 2.0 | 2.25 | 2.5 |
| 9 | C | AA | AA | AA | A | C | D |
| 10 | D | A | AA | A | C | D | D |

Note: manipulation feeling
AA: good
A: rather good
B: ordinary
C: not good
D: very bad With the above technical analyses in mind, although the requisite factors for the present invention resides chiefly in the numerical limitations, the invention relates to the torsional rigidity coefficient K and the ratio (D/d) of the helical spring 3 which consists in a new idea based on a novel conception, and not mere limitations depending on design alterations usually experienced for those versed in the art. It is to be noted that the first article to encounter the blood vessel stricture area is the leading head 4 in which the core elongation 2 has a minimum cross section with the torsional rigidity coefficient K applied as the specified numerical range.

In this instance, as observed in FIG. 1, a semispherical head 12 is secured to a front tip of the core elongation 2 and the helical spring 3 to consolidate the helical spring 3 to the core elongation 2. However, the semispherical head 12 may be omitted when it deems unnecessary to secure the head 12.

The medical guide wire 1 according to the invention which satisfies the requisite factors ensures the high trap load and blocking unfavorable wavy deformation so as to overcome the problems which the prior art counterpart had. This produces the medical guide wire 1 capable of the good maneuverability upon inserting the leading head 4 into the blood vessel which satisfies the numerical requirements regarding the length ratio (a/b) and the torsional rigidity coefficient K.

While there has been described what is at present thought to be preferred embodiments of the invention, it will be understood that modifications may be made therein and it is intended to cover in the appended claims all such modifications which fall within the scope of the invention.

What is claimed is:

1. A medical guide wire comprising:

a core member having a flexible front end portion. rectangular in cross section;

a helical spring wound around the flexible front end portion of the core member;

the core member having a torsional rigidity coefficient of 16 or less in terms of $K \times 10^3$; and the helical spring having a helical diameter-to-line diameter ratio in the range of 2.5~3.5.

where the torsional rigidity coefficient is a divided value of (a maximum torsional stress based on a torsional moment to which the core member is subjected)/(the torsional moment to which the core member is subjected), the helical diameter-to-line diameter ratio is a value of (a mean value of outer and inner diameters of the helical spring)/(a line element diameter of the helical spring).

2. The medical guide wire according to claim 1, wherein a ratio of a vertical length to a lateral length of the front end portion of the core member to which the helical spring is wound is in the range of 1.25~1.75.

3. The medical guide wire according to claim 2, wherein the outer diameter of the helical spring is substantially 0.355 mm.

4. The medical guide wire according to claim 1, wherein the outer diameter of the helical spring is substantially 0.355 mm.

* * * * *